United States Patent [19]
Hendrick et al.

[11] Patent Number: 6,007,848
[45] Date of Patent: Dec. 28, 1999

[54] USE OF 1,4-ANHYDROGLUCITOL/GALACTITOL IN LOW CALORIE FOOD PRODUCTS, AND A METHOD OF PREPARING 1,4-ANHYDRO-DL-GALACTITOL

[75] Inventors: Michael E. Hendrick, deceased, late of Groton, by Martha S. Hendrick, executor; Barry J. Morton, Gales Ferry; Robert J. Rafka, Noank, all of Conn.

[73] Assignee: Cultor Ltd., Helsinki, Finland

[21] Appl. No.: 08/809,674

[22] PCT Filed: Apr. 28, 1995

[86] PCT No.: PCT/IB95/00308

§ 371 Date: Jul. 15, 1997

§ 102(e) Date: Jul. 15, 1997

[87] PCT Pub. No.: WO96/08976

PCT Pub. Date: Mar. 28, 1996

Related U.S. Application Data

[63] Continuation of application No. 08/311,087, Sep. 23, 1994, abandoned.

[51] Int. Cl.$^6$ ........................................... A23L 1/236
[52] U.S. Cl. .............................. 426/3; 426/100; 426/101; 426/548; 426/549; 426/558; 426/559; 426/660; 536/124
[58] Field of Search ................................ 426/3, 100, 101, 426/548, 549, 658, 659, 660, 558, 559; 536/124

[56] References Cited

U.S. PATENT DOCUMENTS

| | | | |
|---|---|---|---|
| 3,895,117 | 7/1975 | Backlund | 426/519 |
| 3,924,006 | 12/1975 | Grylls | 426/24 |
| 3,959,495 | 5/1976 | Lee | 426/24 |
| 3,962,467 | 6/1976 | Burrows | 426/62 |
| 4,297,290 | 10/1981 | Stockburger | 260/410 |
| 4,593,057 | 6/1986 | Stephen et al. | 524/111 |
| 4,810,640 | 3/1989 | Nakamura et al. | 435/25 |
| 4,994,377 | 2/1991 | Nakamura et al. | 435/25 |

FOREIGN PATENT DOCUMENTS

| | | |
|---|---|---|
| 0 092 998 | 11/1983 | European Pat. Off. . |
| 0 131 176 | 1/1985 | European Pat. Off. . |
| 0 347 121 | 12/1989 | European Pat. Off. . |

OTHER PUBLICATIONS

Chen, Z. Sorbitol anhydride fatty acidesters and their polyglycol derivitives, Shipin Kexue (Beijing), 68, pp. 19–22, 1985.

Lukac, J. Isolation of lipids and lipid soluble additives: detection of emulsifiers, Dtsch. Leben sm–Rundsch., 84 (7) p. 217–19, 1988.

*Primary Examiner*—Helen Pratt

[57] ABSTRACT

Low calorie food products that contain highly crystalline bulking agents that impart improved texture and mouthfeel to the food products are described. The food products contain 1,4-anhydroglucitol or 1,4-anhydrogalactitol and a food ingredient. A method of preparing 1,4-anhydro-DL-galactitol comprising heating galactitol in a water-immiscible, high-boiling, reaction-inert medium in the presence of a mineral acid is also described.

22 Claims, No Drawings

USE OF 1,4-ANHYDROGLUCITOL/ GALACTITOL IN LOW CALORIE FOOD PRODUCTS, AND A METHOD OF PREPARING 1,4-ANHYDRO-DL-GALACTITOL

This is a National Stage application under 35 U.S.C. §371 of International Application No. PCT/IB95/00308, filed Apr. 28, 1995 which is a continuation of U.S. Pat. application Ser. No. 08/311,087 filed Sep. 23, 1994, now abandoned.

BACKGROUND ART

The field of art to which this invention is directed is food products, and in particular low calorie food products, low calorie bulking agents, and also methods of preparing low calorie bulking agents.

Many substances are used in the manufacture of foods intended for persons who must restrict their intake of carbohydrates or calories or both. Generally, ingredients which are to be included in these foods must be of low calorific value. Furthermore, the dietetic foods produced with these ingredients must closely resemble calorie-containing foods in texture, taste and physical appearance. In addition, these ingredients must not, of course, present any problems of toxicity to the consumer of the food. Many materials which have been proposed for use in dietetic foods do not satisfy all of these requirements simultaneously.

Where a synthetic sweetener such as saccharin or cyclamate is used in a dietetic food to replace the sugar present in the natural food, the other physical properties, aside from sweetness, which were imparted to the natural food by the sugar must be imparted to the synthetic dietetic food by additional ingredients other than the synthetic sweetener. Some of the additional ingredients suggested for this use are nutritive themselves, and therefore add undesirable calorific value to the food to replace the calorific value contained in the sugar which was removed. Some of these ingredients may also alter the texture or eating qualities of the food so that it becomes unappealing or unwholesome. Finally, these additional ingredients may impart an unnatural color to the food, and, consequently, render it less palatable.

One low calorie food ingredient that has met with acceptance is polydextrose. Polydextrose is a low-calorie food ingredient typically used as a bulking agent to replace higher caloric food ingredients (e.g., sugars, fats) in food compositions. In general, polydextrose is a randomly bonded condensation polymer of dextrose and polycarboxylic acids (e.g., citric acid). There are a variety of polydextroses and these different polydextrose modifications can have different properties as food additives.

Polyols such as sorbitol (D-glucitol) and mannitol have widespread commercial application and are commonly used food ingredients. As a group the acyclic polyols are crystalline bodies covering a wide range in melting point and in taste ranging from faintly sweet to very sweet. The polyols commonly used in foods range in caloric availability from essentially fully caloric (sorbitol) to ca. 50% caloric (mannitol, lactitol). By removal of the elements of water from polyols it is possible to generate a number of cyclic anhydrides, or anhydropolyols.

Dulcitan, which consists mainly of 1,4-anhydrogalactitol is known to be non-metabolizable (Advances in Carbohydrate Chemistry 1, 175 (1945)). At least two other anhydrohexitols (1,4-anhydromannitol and 1,5-anhydro-D-sorbitol) are also said to be nonmetabolizable.

Although such food additives as polydextrose make a significant advance in the field of food products there is a continual search for alternative low-calorie food bulking agents that impart the desired characteristics to food compositions, particularly the combination of low caloric utilization and crystallinity.

SUMMARY OF THE INVENTION

This invention is directed to a low calorie food product that contains a low calorie bulking agent that imparts improved taste qualities to the food product. The food product comprises 1,4-anhydroglucitol or 1,4-anhydrogalactitol and a food ingredient. Particularly preferred bulking agents include 1,4-anhydro-D-glucitol or 1,4-anhydro-D L-galactitol.

Another aspect of this invention is a method of preparing 1,4-anhydro-DL-galactitol comprising heating galactitol in a water-immiscible, reaction-inert medium that has a boiling point of about 175° C. to about 225° C. in the presence of a mineral acid. A particularly preferred mineral acid is phosphoric acid and a particularly preferred medium is undecane.

Yet another aspect of this invention is the novel bulking agent 1,4-anhydro-L-glucitol.

These low calorie food products make a significant advance in the field of food products by providing reduced calorie, highly crystalline, bulking agents that have improved texture and mouthfeel.

Other features and advantages will be apparent from the specification and claims.

DETAILED DESCRIPTION OF THE INVENTION 1,4-Anhydro-D-glucitol may be prepared using the procedure disclosed in Acta Chem. Scand., B35, 441–449 (1981), whereby D-sorbitol is heated with an aqueous mineral acid such as sulfuric acid. The L-enantiomer, 1,4-anhydro-L-glucitol, may be prepared from L-glucitol by an analogous procedure. L-glucitol may be prepared by sodium borohydride reduction of L-glucose. The D and L enantiomers may simply be combined to form a 1,4-anhydro-DL-glucitol mixture.

1,4,-Anhydro-DL-galactitol may be prepared by heating galactitol (i.e., meso-galactitol), preferably at a temperature of about 175° to about 225° C., in a water-immiscible, reaction-inert medium (the solvent has a boiling point of about 175° C. to about 225° C.) in the presence of a mineral acid and preferably removing the water coproduct (e.g., by distillation). Thus, this reaction is performed as a melt which obviates the removal of the water prior to crystallization required by prior processes which used aqueous solvent systems. The use of the water-immiscible, reaction-inert medium described above (i.e., a non-solvent for the reactant and product) facilitates the removal and measurement of water coproduct (formed by the dehydration) as a means of assessing the reaction's progress. This facilitates control of the reaction by reducing the amount of unreacted starting material and polymeric condensation products that are not only difficult to remove but lead to decreased yields.

Preferable solvents include straight chain ($C_{10}$–$C_{14}$) aliphatic hydrocarbons, cyclic hydrocarbons such as cis- and trans-decahydronaphthalene (or mixtures thereof i.e., Decalin®), and aromatic compounds such as p-cymene, 1,3,5-triethylbenzene, 1,2,3,4-tetrahydronaphthalene (Tetralin®), and o-dichlorobenzene. Undecane is the most preferred solvent.

More preferably, 1,4-anhydro-DL-galactitol may be prepared by melting galactitol (m.p.188–191° C.) in refluxing undecane (b.p. 196° C.) in the presence of a catalytic amount of a mineral acid, preferably phosphoric acid, and removing the resulting water formed by the dehydration reaction. Preferably, the amount of acid is less than about 0.5 mole with respect to the galactitol. The resulting product may be purified by standard practice such as recrystallization from, for example, propanol.

1,4-Anhydro-DL-galactitol may be separated into the corresponding D and L enantiomers on the basis of their physical chemical differences by methods known per se, for example, by chromatography and/or derivatization followed by fractional crystallization.

The starting materials for the above described reactions are readily available or can be easily synthesized by those skilled in the art using conventional methods of organic synthesis.

Typical uses for the above described bulking agents include low calorie jellies, jams, preserves, marmalades, and fruit butters; dietetic frozen food compositions including ice cream, ice milk, sherbet and water ices; baked goods such as cakes, cookies, breads, pastries and other foodstuffs containing wheat or other flour; confections (particularly chocolate compositions, chocolate centers, and fudge) and chewing gum; beverages such as soft drinks; sweet sauce, syrups, and toppings; icings; frostings and fillings for baked goods; whipped toppings; puddings; salad dressings; and as bulking agents for dry low calorie sweetener compositions containing cyclamate, saccharin, aspartame, alitame, stevioside, neohesperidin dihydrochalcone, or sucralose.

In the above described food compositions the bulking agents of this invention are combined with appropriate, readily available, food ingredients in suitable proportions according to methods consistent with the standard skill in the art.

For example, the reduced calorie bulking agent replaces some, most, or all of the sugar normally in full calorie recipes, providing body and textural properties to the food that would otherwise be lost. The actual amounts used vary depending on the level of caloric reduction desired, the specific low-calorie sweetener used, and the effects of the bulking agent on processing characteristics, sweetness, flavor, and textural properties of the final food. A wide variety of food formulations incorporate sugar, and thus would benefit by calorie reduction with appropriate use of this invention. Table 1, below, provides an exemplary list of foods in which the bulking agents of this invention could be used.

The actual amount of bulking agent of this invention to be used varies greatly depending on the food type, the kind and type of coingredients, the desired bulk physical properties (texture, viscosity, density, brittleness, etc.) and the selected flavor system of the finished food (e.g., strongly flavored foods such as chocolate frosting have been shown to be acceptable with more than twice as much 1,4-anhydro-D-glucitol as used in a bland vanilla frosting). In general, full calorie food examples cited in Table 1 or found in standard food formularies (e.g., *Food Products Formulary Series*, AVI Publishing Company Inc., Westport, Conn., Vol. 11 1975, Vol. IV 1982) or in cookbook recipes can be simply modified by replacing some or all of the sugar with up to an equivalent amount of bulking agent and adjusting the level of low-calorie sweetener as appropriate to obtain the desired sweetness and textural properties in the finished food. Final use levels are then adjusted by those skilled in the art to yield an optimal balance of flavor, texture, processing ease, and cost. Examples of how much sugar is commonly used in full calorie foods and, therefore, the potential amount of bulking agent required for various foods follow:

TABLE 1

| Food | Typical Sugar Content (Range-Wt. %) | |
|---|---|---|
| | Low | High |
| Peanut Brittle | 58 | 88 |
| Fondant | 58 | 88 |
| Fudge Icing, white | 56 | 84 |
| Cookie filling, chocolate | 51 | 77 |
| Marshallows | 46 | 68 |
| Chocolate Fudge | 42 | 62 |
| Chocolate Icing | 41 | 61 |
| Cream Filling | 33 | 49 |
| Basic Icing | 30 | 46 |
| Cookie Dough (refrigerated) | 26 | 40 |
| Bakers Jelly | 26 | 38 |
| Pralines | 24 | 36 |
| White Layer Cake | 22 | 34 |
| Devil's Food Cake | 21 | 31 |
| Sugar Cookies | 19 | 29 |
| Brownies | 18 | 28 |
| Chocolate Chip Cookies | 18 | 26 |
| Chocolate fudge topping | 15 | 28 |
| Apple Jelly | 14 | 20 |
| Peanut Butter Cookies | 13 | 19 |
| Danish Pastry | 13 | 19 |
| Ice Cream | 10 | 14 |

As discussed above, in actual practice the amount of bulking agents of this invention that can be used will be equal to or less than the sugar levels cited in Table 1. Additional guidelines for the preferred uses of the invention are discussed below.

The highly crystalline bulking agents of this invention are believed to modify the glass transition temperature, melt profiles, viscosity and particle size of semi-solid (including very viscous liquids or syrups and gels) and solid foods and thus contribute to texture, mouthfeel and flavor impact. Thus, these bulking agents are particularly advantageous in high solids, high calorie foods such as fudge, cookie fillings, and frostings.

The term "high solids" food refers to finished foods sufficiently lacking in free water that the subject bulking agent will be, in whole or in part, in a solid crystalline state. The term "high calorie" food specifically refers to those foods in which either sugar or fat comprise a significant portion (e.g., greater than 10%) of the food solids. Hence, the preferred types of food particularly suitable for use of the crystalline bulking agent of this invention are: crystallized sugar foods consisting largely of sugar and flavorings such as hard candy; solid or semi-solid or aerated foods in which sugar syrups comprise the continuous phase and fats or other solids the discontinuous phase, e.g., icings, sweet glazes, and fillings such as marzipan, toffees, caramels, fudges, fondants, filling creams, fruit syrups, jellies, marshmallows; and solid or semi-solid or aerated foods containing sugar in which fat is the continuous phase and sugar is the discontinuous phase e.g., molded chocolates, chocolate coatings, nougats, truffles, wafer and biscuit fillings, dairy butters and yogurt. Less easily classified but also suitable are high solids baked goods (e.g., sugar cookies, date nut squares, etc.) and frozen dairy desserts, where water, sugar, and/or bulking agent are crystallized to various degrees during the freezing process.

The general comments given above for generic substitution of bulking agents for sugar apply in the preferred foods described above along with the following more specific guidelines. Crystallized sugar foods such as hard candies generally contain very high sugar levels (e.g., greater than 50%) and therefore afford texture, flavor (e.g., sweetness), and melt properties which preferably are not completely simulated by equivalent levels of bulking agent. In applications where sugar levels exceed 50% of the finished food, maximum use level of the crystalline bulking agent is preferably limited to 25% of the finished food. Actual use levels vary depending on the type, texture, melt and flavor requirements of the finished food.

The second and third types of preferred foods described above often share common ingredients (sugar or corn syrup, milk fat and/or confectionery fats (e.g., cocoa butter, lauric fats, fractionated, interesterified and hydrogenated vegetable or tropical oils), water, and flavoring), but are processed differently to yield foods with different ratios of sugar to fat to air and different particle sizes. Component ratio and particle size distribution directly affect texture and melt profile of the finished product. Particle size is generally controlled by carefully adjusting the rate of product cooling over a specific temperature range and/or by one or more milling processes with rapid cooling and/or finer milling generally yielding food products with smoother texture. Further processing details can be obtained from numerous sources such as Inglett's *Fabrication of Foods*, Vol. IV of the *Food Product Formulary Series* cited above.

Representative examples of foods incorporating the above-described crystalline bulking agents are included. While these examples set forth proportions of the crystalline bulking agents which are suitable for the particular dietetic food involved, the quantities of crystalline bulking agents required for other food compositions encompassed by this invention can be readily determined. Standard manufacturing procedures are applicable to each of the recipes for dietetic foods which are given in the examples.

It should be understood that the invention is not limited to the particular embodiments described herein, but that various changes and modifications may be made without departing from the spirit and scope of this novel concept as defined by the claims.

EXAMPLE 1

Thousand Island Dressing

Total weight 100 Grams.

| Ingredients | Percent |
|---|---|
| Water A (for xanthan and alginate hydration) | 6.00 |
| Xanthan gum (Keltrol F)[1] | 0.15 |
| Propylene glycol alginate (Kelcoloid LVF)[1] | 0.15 |
| Modified food starch (Ultra-Tex 4)[2] | 2.50 |
| 1,4-anhydro-D-glucitol | 6.00 |
| Maltrin M-200 (corn syrup solids)[3] | 4.00 |
| Salt | 1.50 |
| Sugar | 15.00 |
| Seasoning blend (Wisconsin Spice, Pfizer Inc, low fat type)[4] | 2.00 |
| Titanium dioxide[5] | 0.10 |
| Potassium sorbate | 0.10 |
| Sodium benzoate | 0.10 |
| Monosodium glutamate | 0.15 |
| Vinegar (50 grain white distilled) | 16.00 |
| Tomato paste (hot break) | 5.00 |
| Veltol® (1% w/w H$_2$O)[4] | 0.50 |
| Pickle relish (sweet) | 5.50 |
| FD&C yellow #5 (0.10% w/w H$_2$O)[5] | 0.15 |
| FD&C yellow #6 (1.0% w/w H$_2$O)[5] | 0.01 |

-continued

| Ingredients | Percent |
|---|---|
| Egg yolks (frozen 10% salt)[6] | 2.00 |
| Soybean oil | 9.25 |
| Polysorbate 60[7] | 0.10 |
| Water B | 23.74 |
| TOTAL | 100.00 |

[1]Kelco
[2]National Starch and Chemical Corporation
[3]Grain Processing Corporation
[4]Wisconsin Spice, Inc.
[5]Warner Jenkinson Company
[6]Egg Corporation of America
[7]ICI Chemical Corporation Xanthan gum and alginate were prehydrated in water A for 15 minutes with occasional stirring. Water B was added to the mixer. The dry ingredients, except for the pickle relish, were added. The mixture was sheared for two minutes. The sides were scraped and the mixture was sheared for two more minutes. The mixture was homogenized using a colloid mill (i.e., Greerco Model W250) and the pickle relish was stirred in after milling. A Cuisinart food processing center with a 1 kg batch size was used to mix the ingredients.

EXAMPLE 2

Vanilla Frosting

Total Weight 100 Grams

| Ingredients | Percent |
|---|---|
| Sugar, 10X | 61.57 |
| 1,4-anhydro-D-glucitol | 8.71 |
| Powdered non-fat dry milk | 8.59 |
| Solka-Floc 900[1] | 1.00 |
| Vegetable shortening (Creamtex)[2] | 4.50 |
| Dur-Em 114[2] | 4.50 |
| Water | 9.36 |
| Avicel RC 591 F[3] | 0.77 |
| Vanilla extract | 1.00 |
| TOTAL | 100.00 |

[1]Fiber Sales & Development Corp.
[2]Van Den Bergh
[3]FMC

The sugar, 1,4-anhydro-D-glucitol, powdered non-fat dry milk and Solka-Floc 900 were blended and mixed for 3 minutes at speed 1 in a KitchenAid mixer (Model K5SS). The vegetable shortening and Dur-Em 114 were added to the mixture and mixed for 3 minutes at speed 1. The sides of the mixer were scraped down and the mixture was mixed for 1 minute at speed 2. The Avicel RC 591F was added to the water slowly and mixed with an overhead stirrer with increasing speed as the Avicel was added. The Avicel solution was added to the first mixture and mixed on speed 2 until a frosting was formed, followed by additional mixing for 2 minutes at speed 4. The vanilla extract was added to the mixture with subsequent mixing for 1 minute at speed 4. The sides of the mixture were scraped down followed by additional mixing for 30 seconds at speed 4.

EXAMPLE 3

Chocolate Frosting

Total Weight 100 Grams

| Ingredients | Percent |
| --- | --- |
| Vegetable shortening (Creamtex)[1] | 6.00 |
| Dur-Em 114[1] | 1.90 |
| Polysorbate 60[2] | 0.10 |
| Sugar, powdered | 41.00 |
| 1,4-anhydro-D-glucitol | 26.00 |
| Avicel, PH-101[3] | 4.00 |
| Cocoa powder, D-11-SB[4] | 2.70 |
| Chocolate Flavor | 0.30 |
| Salt | 0.25 |
| Ultratex 4[1] | 0.80 |
| Aspartame[6] | 0.15 |
| Veltol® | 100 ppm |
| Water | 15.40 |
| Pectin[8] | 0.75 |
| Vanilla extract 1X (#29 pure k)[8] | 0.65 |
| TOTAL | 100.00 |

[1] Van Den Bergh
[2] Tweeg, Inc.
[3] FMC Corporation
[4] De Zaan, Inc.
[5] Tastemaker, #264907
[6] NutraSweet
[7] Hercules, BB Rapid Set
[8] Virginia Dare The vegetable shortening, Dur-Em 114 and polysorbate 60 were combined and melted. The powdered sugar, 1,4-anhydro-D-glucitol, Avicel, cocoa powder, chocolate flavor, salt, Ultratex, aspartame and veltol were combined and added to the first mixture. The combined mixture was blended evenly in a KitchenAid electric mixer (Model K5SS) on low speed for two minutes. The dry ingredients were sifted as necessary if there was lumping. The pectin was added slowly to water and the vanilla was stirred in to the pectin water solution. The pectin vanilla mixture was added to the dry ingredients and the combined mixture was mixed on low speed until the ingredients were moist followed by mixing for 4 minutes at a speed of 6 to 8.

EXAMPLE 4

Chocolate Syrup

Total Weight 100 Grams

| Ingredients | Percent |
| --- | --- |
| Cocoa, Dutched[1] (10–12% fat) | 10.00 |
| Salt | 0.07 |
| Vanillin | 0.05 |
| Xanthan gum | 0.05 |
| 1,4-anhydro-D-glucitol | 34.98 |
| High fructose corn syrup[2] | 31.98 |
| Water | 22.85 |
| Aspartame | 0.025 |
| TOTAL | 100.00 |

[1] De Zaan type D-11-V
[2] American Maize Products Co. - Tru-Sweet 42

The cocoa, salt, vanilla and xanthan gum were blended together. The 1,4-anhydro-D-glucitol, high fructose corn syrup and water were mixed. The two mixtures were combined and aspartame was added followed by mixing until the mixture was smooth and homogeneous with a lab dispersator.

EXAMPLE 5

1,4-Anhydro-D-Glucitol

The procedure below was based very closely on the preparation of K. Bock, C. Pedersen, and H. Thogersen (*Acta Chem. Scand Ser. B,* 35, (1981) 441–449.)

D-Glucitol (Aldrich, 1150 g, 6.31 mol) was suspended in aqueous 3M $H_2SO4$ (550 mL) and heated at reflux with stirring under $N_2$ overnight. The dark brown solution was cooled and neutralized using Amberlite® IRA-93 resin (OH-, ~4 L) Rohm and Haas, (Phil., Pa.). The resin was removed by filtration; the filtrate was decolorized using activated carbon (4 g) which was subsequently removed by filtration.

Water was evaporated from the solution using a rotary evaporator (bath temp =80° C.). Absolute ethanol (1 L) was added; gentle warming was required to dissolve the colorless, viscous residue. The solvent was removed under aspirator pressure (bath temp =60° C.) which effected crystal formation. Additional ethanol (1.5 L) was added; the solid-liquid mixture was concentrated under aspirator pressure until no additional distillate was obtained.

The residue was dissolved in absolute ethanol (1.5 L) and heated to effect dissolution. The mixture was cooled slightly, seeded, and stirred overnight at ambient temperature. The mixture was then cooled to 0 ° C. and vacuum filtered using a Buchner funnel. Solids were re-pulped in absolute ethanol (0.5 L, -5° C.) then re-filtered and rinsed with additional cold ethanol (0.5 L).

Solids were dried on a Buchner funnel under $N_2$, then ground (mortar and pestle) and dried on the rotary evaporator (high vacuum, 60° C. bath) for 4 hours. The final weight of the 1,4-anhydro-D-glucitol was 459 g (44.3%). HPLC indicated that the major impurity was residual sorbitol, ~0.8%). Solids melted between 113 and 114.5° C.; a doubly recrystallized sample melted between 114 and 115° C. and exhibited a rotation of -22.9° [c=5.4, $H_2O$, lit=-22.4° at the same concentration, see Bock et al.).

The above preparation was alternately performed using both Duolite® A-192L and Amberlite® IRA 400 (both OH-) Rohm and Haas (Phil., Pa.) as neutralization resins and n-butanol and 2-propanol as recrystallization solvents.

EXAMPLE 6

1,4-Anhydro-DL-Galactitol

Galactitol (Aldrich, 40 g, 220 mmol) was suspended in undecane (200 mL), acidified with $H_3PO_4$ (50 mL, 0.4 mmol), and heated to reflux under $N_2$. Water (4.4 mL, 244 mmol, 1.1 equiv) was collected in a Dean-Stark trap over 1 hour. The reaction was cooled and the undecane decanted. The resulting dark syrup was rinsed with hexane and dried under a stream of $N_2$.

A small portion of the crude syrup was partially dissolved in refluxing acetonitrile. The resulting mixture was slowly cooled to ambient temperature and left undisturbed overnight. Fine needles were collected from the sides of the flask for use as seed crystals.

The remaining crude syrup was dissolved in 1-propanol (100 mL), treated with Darco® KB-B activated carbon (2 g), and heated to reflux for 1 h. Upon cooling to ambient temperature, the mixture was filtered through a Celite® pad and the filtrate concentrated in vacuo to a weight of 100 g. The solution was seeded, then stirred at ambient temperature overnight. The resulting crystal-containing mixture was cooled to −4° C. over 8 hours then stirred an additional 24 hours at this temperature. Crystals were isolated by vacuum filtration. The resulting filter cake was rinsed with cold 1-propanol (50 mL); additional washing was performed with ether (100 mL) and pentane (100 mL) to aid in the removal of residual alcohol.

Drying under high vacuum yielded 1,4-anhydro-DL-galactitol (22.3 g, 61.9%); mp 69.5–71° C.; TGA (1% loss at 209° C.); ms calc'd (M+H) 165.0759 (obs'd 165.0764); IR (KBr) 3290, 2994, 2960, 2861, 1354, 1210, 1132, 1088, 1068, 986, 917, 876, 742, and 505 cm$^{-1}$. $^1$H NMR: δ3.59 (dd, 1 H, $J_{6a,6b}$ 11.8, $J_{5,6b}$ 7.3, H-6b), 3.68 (dd, 1 H, $J_{5,6a}$ 4.3, H-6a), 3.71 (app-t, 1 H,$J_{3,4}$=$J_{4,5}$ 4.8, H-4), 3.81, (m, 2 H, H-1b, H-5), 3.97 (dd, 1 H, $J_{1a,1b}$ 10.1, $J_{1a,2}$ 4.7, H-1a), 4.10 (ddd, 1 H, $J_{2,3}$ 2.7, $J_{3,5}$ 0.9 Hz, H-3), 4.21 (d app-t, 1 H, H-2). The structure was additionally confirmed by X-ray crystallography.

The above preparation was also performed using Tetralin® as an alternative solvent and with methanesulfonic acid and toluenesulfonic acid as alternate acid catalysts. The above preparation was also performed using cellosolve, ethanol, dimethoxyethane, 2-propanol, ethanol/methyl tert-butyl ether, n-butanol, dioxane, and acetonitrile as alternative recrystallization solvents.

What is claimed is:

1. A food product containing a low calorie bulking agent comprising:
   a. 1,4 anhydroglucitol or 1,4-anhydrogalactitol; and
   b. a food ingredient.

2. The food product as recited in claim 1 wherein said low calorie bulking agent is 1,4 anhydro-DL-glucitol.

3. The food product as recited in claim 2 wherein said low calorie bulking agent is 1,4 anhydro-D-glucitol.

4. The food product as recited in claim 3 wherein said food product is a high calorie, high solids, food product.

5. The food product as recited in claim 4 wherein said food product is a baked good.

6. The food product as recited in claim 4 wherein said food product is a confection.

7. The food product as recited in claim 4 wherein said food product is a frozen dessert.

8. The food product as recited in claim 4 wherein said food product is a chewing gum.

9. The food product as recited in claim 4 wherein said food product is a baked goods frosting or a baked goods filling.

10. The food product as recited in claim 2 wherein said low calorie bulking agent is 1,4 anhydro-L-glucitol.

11. The food product as recited in claim 1 wherein said low calorie bulking agent is 1,4-anhydro-DL-galactitol.

12. The food product as recited in claim 11 wherein said low calorie bulking agent is 1,4-anhydro-D-galactitol.

13. The food product as recited in claim 11 wherein said low calorie bulking agent is 1,4-anhydro-L-galactitol.

14. The food product as recited in claim 11 wherein said food product is a high calorie, high solids, food product.

15. The food product as recited in claim 14 wherein said food product is a baked good.

16. The food product as recited in claim 14 wherein said food product is a confection.

17. The food product as recited in claim 14 wherein said food product is a frozen dessert.

18. The food product as recited in claim 14 wherein said food product is a chewing gum.

19. The food product as recited in claim 14 wherein said food product is a baked goods frosting or a baked goods filling.

20. A method of preparing 1,4-anhydro-DL-galactitol comprising:
   heating galactitol in a water-immiscible, reaction-inert medium that has a boiling point of about 175° C. to 225° C. in the presence of a mineral acid.

21. The method as recited in claim 20 wherein said mineral acid is phosphoric acid and said medium is undecane.

22. The method as recited in claim 21 wherein said galactitol is refluxed in said undecane and water is removed.

* * * * *